(12) United States Patent
Lang et al.

(10) Patent No.: US 8,496,004 B2
(45) Date of Patent: Jul. 30, 2013

(54) DEVICE FOR EVACUATING BREATHING GAS FROM THE INTERIOR OF A BREATHING MASK, AND BREATHING MASK ARRANGEMENT COMPRISING SAID DEVICE

(75) Inventors: Bernd Lang, Gräfelfing (DE); Achim Biener, Aufkirchen (DE)

(73) Assignee: Resmed R&D Germany GmbH, Martinsried (DE)

( * ) Notice: Subject to any disclaimer, the term of this patent is extended or adjusted under 35 U.S.C. 154(b) by 1180 days.

(21) Appl. No.: 11/632,667

(22) PCT Filed: Aug. 2, 2005

(86) PCT No.: PCT/EP2005/008372
§ 371 (c)(1),
(2), (4) Date: Jan. 17, 2007

(87) PCT Pub. No.: WO2006/015772
PCT Pub. Date: Feb. 16, 2006

(65) Prior Publication Data
US 2008/0066756 A1 Mar. 20, 2008

(30) Foreign Application Priority Data

Aug. 2, 2004 (DE) .................. 10 2004 037 344
Oct. 1, 2004 (DE) .................. 10 2004 048 006

(51) Int. Cl.
*A62B 18/02* (2006.01)
*A62B 9/04* (2006.01)
(52) U.S. Cl.
USPC ............ 128/205.25; 128/202.27; 128/206.21; 128/912

(58) Field of Classification Search
USPC .......... 128/857, 863, 200.24, 205.25, 206.21, 128/207.12, 202.27, 206.27, 206.28, 207.11, 128/207.18, 912
See application file for complete search history.

(56) References Cited

U.S. PATENT DOCUMENTS

| 4,462,397 A | 7/1984 | Suzuki |
| 5,921,239 A * | 7/1999 | McCall et al. ........... 128/205.25 |

(Continued)

FOREIGN PATENT DOCUMENTS

| DE | 197 57 703 | 10/1999 |
| DE | 200 05 346 U1 | 6/2000 |

(Continued)

OTHER PUBLICATIONS

German Search Report for Application No. 10 2004 037 344.2, May 17, 2005, with English Translation, 7 pages.

(Continued)

*Primary Examiner* — Justine Yu
*Assistant Examiner* — Valerie L Skorupa
(74) *Attorney, Agent, or Firm* — Nixon & Vanderhye P.C.

(57) ABSTRACT

A diversion device is provided for diverting breathing gas, which is laden with $CO_2$, from a pressurized region of an arrangement that includes a breathing mask and serves for delivering a breathing gas at a pressure level that is above the ambient pressure. The device has a tubular stub structure which defines a breathing gas conduit that extends between an inlet cross section on the hose side and an outlet cross section on the mask side, and which is provided, in a region located between the inlet cross section and the outlet cross section, with an outflow orifice portion by way of which the breathing gas to be carried reaches the environment. In a region located between the outflow orifice portion and the outlet cross section on the mask side of the breathing gas conduit, a double-walled structure that surrounds the breathing gas conduit is embodied for sampling the breathing gas to be carried away from a mask interior, while largely circumventing the breathing gas conduit.

16 Claims, 6 Drawing Sheets

U.S. PATENT DOCUMENTS

| | | | |
|---|---|---|---|
| 5,937,851 A | 8/1999 | Serowski et al. | |
| 6,112,745 A | 9/2000 | Lang | |
| 6,691,707 B1 | 2/2004 | Gunaratnam et al. | |
| 6,823,869 B2 | 11/2004 | Raje et al. | |
| 6,907,882 B2 | 6/2005 | Ging et al. | |
| 7,089,939 B2 * | 8/2006 | Walker et al. | 128/205.24 |
| 7,316,230 B2 | 1/2008 | Drew et al. | |
| 2003/0094177 A1 | 5/2003 | Smith et al. | |

FOREIGN PATENT DOCUMENTS

| | | |
|---|---|---|
| DE | 100 14 178 C2 | 9/2001 |
| EP | 1 138 340 | 10/2001 |
| EP | 11 38 340 B1 | 10/2001 |
| EP | 1 362 610 | 11/2003 |
| WO | 03/059427 | 7/2003 |

OTHER PUBLICATIONS

International Search Report for PCT/EP2005/008372 mailed Nov. 4, 2005 (English and German).

Office Action dated Apr. 22, 2013 issued in European Patent Application No. 05774404.7 and Entfish Translation, 5 pp.

* cited by examiner

DEVICE FOR EVACUATING BREATHING GAS FROM THE INTERIOR OF A BREATHING MASK, AND BREATHING MASK ARRANGEMENT COMPRISING SAID DEVICE

This application is the US national phase of international application PCT/EP2005/008372 filed 2 Aug. 2005, which designated the U.S. and claims priority to DE 10 2004 037 344.2 filed 2 Aug. 2004, and DE 10 2004 048 006.0 filed 1 Oct. 2004, the entire contents of each of which are hereby incorporated by reference.

The invention relates to a device for diverting exhaled, i.e. $CO_2$-laden breathing gas from a breathing gas supply system. The invention also relates to a breathing mask arrangement formed with the inclusion of such a device.

Particularly for treating sleep-related breathing problems, it is known to deliver a breathable gas, such as ambient air, to a patient at a pressure level that at least in some phases is above the ambient pressure. As a result, it is possible to bring about an effect known as pneumatic splinting in the region of the upper airways, by means of which any obstructions in this region can be averted. The delivery of a breathable gas at a level that is above the ambient pressure can be therapeutically advantageous in still other ways besides the treatment of sleep-related breathing problems.

In the known systems, the breathing gas delivery is done by using a flexible breathing gas line and a breathing mask applied to the patient. In the case where affected persons need therapy, such systems for breathing gas delivery are typically worn during the entire sleeping phase, without special supervision. Reliably diverting the $CO_2$ contained in the exhaled breathing gas is of particular importance.

From U.S. Pat. No. 6,112,745 of the present Applicant, an adapter provided for disposition between a breathing mask and a breathing gas hose is known that includes two detachably joined-together tube segments that are rotatable relative to one another about the longitudinal axis of an adapter; the tube segments are dimensioned such that in the region of the joint an annular gap is created, by way of which used breathing gas can be continuously diverted, and thus a permanent breathing gas exchange is made possible in the region of the breathing mask.

From WO 03-059427, also of the present Applicant, a breathing mask is known in which a diversion of partly used breathing gas from the mask interior is done through outflow openings, which are located in a wall region of the breathing mask that, in the application position of the breathing mask, is diametrically opposite the nostrils of a user.

The known connectors for diverting breathing gas aim at enabling an adequate outflow of breathing gas with little noise and with the least possible disturbance of both the patient and a person who might be lying next to the patient.

The object of the invention is to disclose embodiments that offer further advantages in diverting used breathing gas from the overpressure region of a breathing gas delivery system.

This object is attained, in a first aspect of the invention, by a diversion device for diverting breathing gas, which is laden with $CO_2$, from a pressurized region of an arrangement that includes a breathing mask and serves for delivering a breathing gas at a pressure level that is above the ambient pressure, having a tubular stub structure, which defines a breathing gas conduit that extends between an inlet cross section on the hose side and an outlet cross section on the mask side, and which is provided, in a region located between the inlet cross section and the outlet cross section, with an outflow orifice portion by way of which the breathing gas to be carried reaches the environment, wherein, in a region located between the outflow orifice portion and the outlet cross section on the mask side of the breathing gas conduit, a double-walled structure that surrounds the breathing gas conduit is embodied for sampling the breathing gas to be carried away from a mask interior, while largely circumventing the breathing gas conduit.

As a result, it advantageously becomes possible, even at low breathing gas pressures, to attain an appropriate exchange effect in a way that is advantageous in terms of the profile of the flow prevailing in the mask interior. Especially advantageously, it is attained that any breathing gas introduced into the mask interior beyond what is needed does not cause any drafts. Moreover, advantages are attained in terms of the reduced clearance.

The double-walled structure is preferably formed by a sleeve element, which is inserted into or placed onto a main washing element body. The sleeve element and the main washing element body are preferably made from a sterilizable plastic material. The sleeve element and the main washing element body are preferably detachably joined together. For joining the main washing element body and the sleeve element, plug-type or detent structures can be provided, by which it becomes possible to couple the two structures in a suitable position.

In an especially preferred embodiment of the invention, the sleeve element and the main washing element body are embodied such that the sleeve element protrudes past the main washing element body in the region of the mask-side outlet cross section. As a result, it becomes possible for the gas to be carried out of the interior of a breathing mask to be sampled in a region of the supply conduit located downstream of the end portion penetrating into the mask interior, and hence to achieve an especially favorable rinsing of the interior.

It is possible to form air guide structures in the region of the double-walled structure that produce a required air resistance. These air guide structures may be embodied by ribs, particularly forming labyrinth structures in or on the sleeve element and/or the main washing element body. It is possible to embody these air guide structures such that by way of the disposition of the sleeve element relative to the main washing element body, the flow resistance and thus the air quantity flowing out are adjustable. These ribs or protrusions can be disposed such that by means of them, the gap width of the airway formed in the double-walled structure is defined.

The main body is preferably provided with a rotary adapter structure or rotary stub structure for rotatably supporting a rotary stub element. The rotary adapter structure preferably has a plurality of yielding legs, embodied integrally with the main washing element body, with detent lugs. The legs preferably form part of the breathing gas conduit wall.

The double-walled structure is preferably embodied such that it defines a gap with a radial gap height in the range from 0.3 to 3.2 mm.

With respect to a breathing mask arrangement, the above object is also attained by a breathing mask arrangement having a mask interior surrounded by a basic mask body and a sealing lip device, wherein the basic mask body has a connection portion for receiving a tubular stub structure which defines a breathing gas conduit that extends between an inlet cross section on the hose side and an outlet cross section on the mask side and which is provided, in a region located between the inlet cross section and the outlet cross section, with an outflow orifice portion by way of which the breathing gas to be carried reaches the environment, wherein, in a region located between the outflow orifice portion and the outlet cross section on the mask side of the breathing gas conduit, a double-walled structure that surrounds the breathing gas conduit is embodied for sampling the breathing gas to be carried away, with complete or extensive disconnection of the sampled air stream from the conduit region, serving to store breathing gas, of the tubular stub structure.

Preferably, the tubular stub structure is seated in the region of the double-walled structure in the connection portion of the basic mask body.

The definition of "largely circumventing the breathing gas conduit" is understood in particular to mean sampling connectors in which an inlet region, by way of which the gas to be carried away flows toward the conduit (reference numeral 12) thanks to the double-walled structure, is located outside the main conduit. However, by using the double-walled structure of the invention, advantages are still attained even if the inlet gap is offset inwardly into the main conduit by no more than 10% or approximately 8 mm from the mask-side edge of the orifice of the main conduit.

Further details and characteristics of the invention will become apparent from the ensuing description in conjunction with the drawings. Shown are:

FIG. 3b, a radial sectional view for explaining the conduit cross sections provided in the variant of FIG. 3a;

Figure 1:
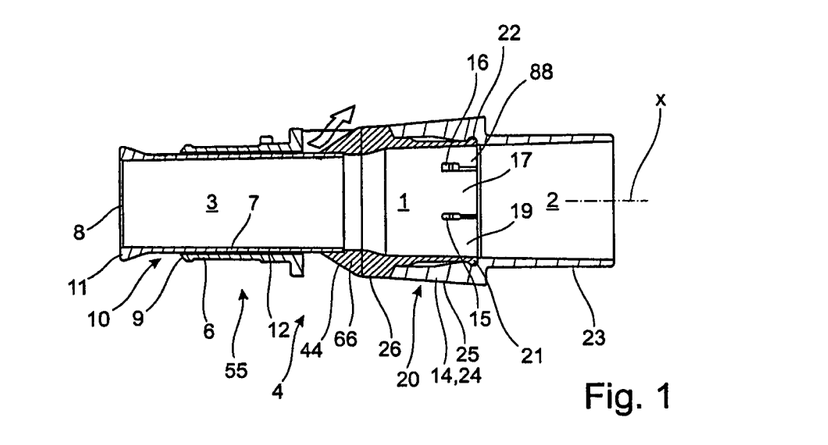
FIG. 1, a sectional view through a device according to the invention for diverting $CO_2$-laden breathing gas.

The device shown in FIG. 1 is a multi-part tubular stub structure, which defines a breathing gas conduit 1 intended for delivering a breathable gas to a breathing mask. The breathing gas conduit extends between an inlet cross section 2 on the hose side and an outlet cross section 3 on the mask side. This tubular stub structure is provided with an outflow orifice portion 4 by way of which breathing gas to be carried away reaches the environment. In a region extending between the outflow orifice portion 4 and the mask-side outlet cross section 3, a double-walled structure 5 surrounding the breathing gas conduit 1 is embodied, which serves to sample a breathing gas to be carried away from the region of a breathing mask arrangement; the double-walled structure is embodied such that this sampling is done in the region of the mask-side outlet cross section 3 or in a region axially upstream of this mask-side outlet cross section 3.

In this exemplary embodiment, the double-walled structure 5 is formed of a tubular stub portion 6 and a sleeve element 7. The tubular stub portion 6 forms part of a main washing element body 66, which is molded from a thermoplastic material and in which the walls required for furnishing the outflow orifice portion 4 are furnished.

The sleeve element 7, in this exemplary embodiment, is inserted into the main washing element body in such a way that the aforementioned double-walled structure 5 is formed in the conduit region extending between the mask-side outlet region 3 and the washing orifice portion 4. The sleeve element 7 and the tubular stub portion 6 are dimensioned such that between the outer circumferential region of the sleeve element 7 and the inner circumferential wall of the tubular stub portion 6, an interstice remains that functions as a conduit by way of which the air to be diverted from the interior of the breathing mask can advance to the outlet orifice portion 4.

In this exemplary embodiment, the sleeve element 7 is embodied such that it is insertable detachably into the main washing element body 66. The sleeve element 7 in this exemplary embodiment is dimensioned in terms of its axial length such that its terminal circumferential face 8, protruding into the mask interior, protrudes axially past a terminal circumferential face or end face 9 of the tubular stub portion 6. As a result, an axial offset is attained between the mask-side orifice of the breathing gas conduit 1 and the inlet gap region 10 of the double-walled structure 5.

In the region of the terminal circumferential face 8, the sleeve element 7 is provided with a circumferential bead 11 by means of which even further-improved flow conditions in terms of rinsing a mask interior are created.

The gap formed in the region of the double-walled structure 5 is dimensioned such that it has a flow resistance that while not excessively high still adequately throttles the outflow of the breathing gas to be diverted toward the outlet orifice portion 4. In the region of the inner wall of the tubular stub portion 6 of the main washing element body 66 and/or on the outer circumferential wall of the sleeve element 7 inserted into the main washing element body 66, structures such as bumps or small individual protrusions may be provided, by which a required minimum gap size of the conduit 12 formed in the double-walled structure 5 is assured.

In the region of the outflow orifice portion 4, an outflow ramp 44 is preferably embodied, by which the breathing gas flowing to the outflow orifice portion 4 via the conduit 12 is deflected. The outflow ramp 44 is preferably embodied such that the emerging breathing gas still conforms, over a travel distance of approximately 7 cm, to the circumferential wall of the main washing element body 66 or a rotation cuff 14 rotatably placed on it, and a breathing gas hose that adjoins the rotation cuff in turn and is not further shown here.

The main washing element body 66 has a plurality of spring legs 17, 18, 19 being separated from one another by axial recesses 15, 16. These spring legs form part of a rotary bearing portion 20 of the main washing element body 66, onto which the rotation cuff 14 is placed detachably, such that the rotation cuff is rotatable about the longitudinal axis X of the main washing element body 66. Detent lugs 21, 22 are embodied on the spring legs 17, 18, 19 and are capable of snapping into an inner circumferential groove embodied correspondingly complementary to the lugs in the rotation cuff 14.

The rotation cuff 14 is embodied such that it has a hose mounting stub 23 which is embodied slightly conically and intended for placing a flexible breathing gas hose onto it, and a rotation cuff portion 24 which is intended for placement onto the spring legs 17, 18, 19 or a corresponding portion of the main washing element body 66. The rotation cuff portion 24 is embodied slightly conically in the region of its outer circumferential surface 25 and widens from a circumferential wall 26, bordering on the outflow ramp 44, to the outer diameter of the hose to be placed onto the hose mounting stub 23.

Although it cannot be seen in this view, it is possible for the device of the invention to be embodied in the region of the outflow orifice portion 4 such that a diversion of the used breathing gas to the environment takes place not over the entire circumference of the main washing element body 66 but only over a selected angular range of, for instance, 270°, so that an exposure of the bridge of the nose, forehead, or head region of a mask user to the diverted breathing gas is avoided. The outflow of air can accordingly be influenced by shielding structures mounted on the main washing element body 66 or local blockage of the conduit 12.

The device according to the invention for coupling a breathing gas hose to a breathing mask while simultaneously furnishing a rinsing path intended to divert partially used breathing gas is shown in an enlarged manner in this view. This device is preferably dimensioned such that the inside diameter of the breathing gas conduit amounts to approximately 14 to 22 mm, and the total length of this device, including the mounting stub 23 of the rotation cuff preferably amounts to approximately 5.5 to 10 cm.

Particularly by way of the main washing element body 66, other structures, some of them also discussed below in conjunction with detailed views, are furnished, by means of which further conduits, such as pressure measuring conduits or conduits for delivering oxygen or measuring the oxygen content of the air, can be furnished.

Figure 2:
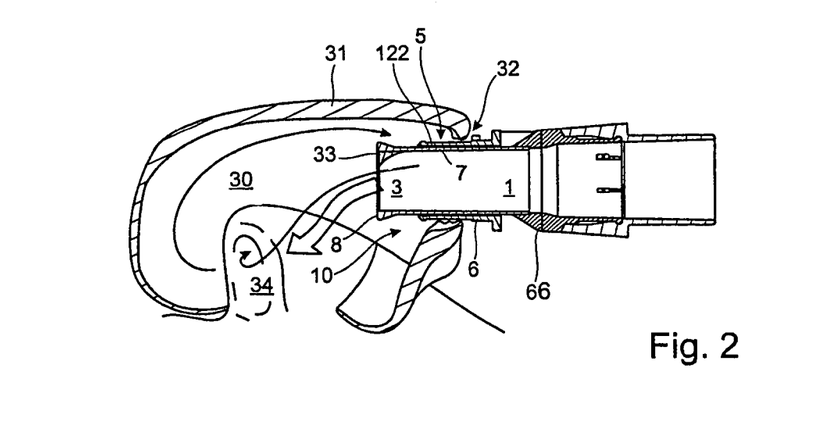
FIG. 2, a sectional view for explaining the use of the breathing mask arrangement embodied according to FIG. 1.

FIG. 2 shows in the form of a simplified sectional view how a device according to the invention—essentially embodied as described above—can be coupled to a basic mask body 31 that defines a breathing mask interior 30. In this exemplary embodiment, the basic mask body 31 is made from an elastomer material, in particular silicone rubber, and includes a connection portion 32 which is elastically widenable in the radial direction and in which the device of FIG. 1 can be inserted so that it is adequately firmly seated. The geometry of the basic mask body 31 in the region of the connection portion 32 and the outer geometry of the tubular stub portion 6 of the main body 66 are preferably adapted to one another such that, as a result, a coupling of the two components that is adequate in terms of sealing and load-bearing capacity is obtained.

In the arrangement shown here, breathing gas flowing in via the breathing gas conduit 1 can flow via the mask-side outlet cross section 3, formed here by the sleeve element 7, into the breathing mask interior 30, as represented by the arrow symbol P2. The inflow of breathing gas to the breathing mask interior 30 may be varied, as shown here, by means of air guide structures 33.

In this exemplary embodiment, the $CO_2$-laden air that during an exhalation phase reaches the breathing mask interior 30 via the nostrils 34 of a user can flow out into the conduit 12 formed by the double-walled structure 5, via a gap region 10 located downstream of the terminal circumferential face 8. Through the mask-side outlet cross section of the breathing gas conduit 1 which is offset toward the nostrils 34 by using the sleeve element 7, and the inlet gap region 10 axially recessed from this forward-shifted mask-side outlet cross section 3, an especially advantageous rinsing of the breathing mask interior 30 and an attendant advantageous diversion of the $CO_2$-laden breathing gas, emerging from the nostrils 34 in the exhalation phase, from the breathing mask interior 30 is attained.

Figure 3A:
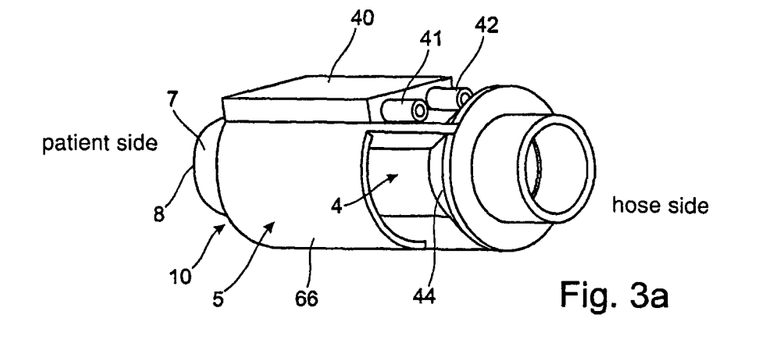
FIG. 3a, a perspective view of a further variant of a device according to the invention.

In FIG. 3a, a variant of a device according to the invention is shown in a perspective conceptual view; in it, by means of a double-walled structure 5, an axial offset is attained between the sampling point (inlet gap region 10) intended for diverting the $CO_2$-laden breathing gas, and the terminal circumferential face 8 of the sleeve element 7. In this exemplary embodiment, the main washing element body 66 is provided with further structures 40 forming air guide conduits through which hose connection stubs 41, 42 are furnished, through which a breathing gas pressure measurement or a delivery of gas to or diversion of gas from the inner region of a breathing mask (see FIG. 2) can be accomplished. In this exemplary embodiment as well, an outflow ramp 44 is provided in the region of the outflow orifice portion 4, and by way of this ramp the outflowing breathing gas can advantageously be deflected toward the outside.

Figure 3B:
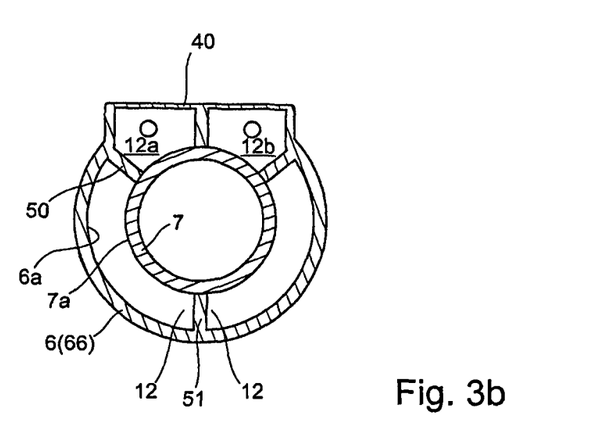

In FIG. 3b, an axial sectional view of the device of FIG. 3a is shown. As can be seen from this view, the sleeve element 7 is inserted into the tubular stub portion 6 that forms part of the main washing element body 66. Between the inner wall 6a and the outer circumferential surface 7a of the sleeve element 7, a conduit 12 as already described above is defined, which in this exemplary embodiment is divided longitudinally by axial ribs 50, 51, 52. In the region of the structure 40 that is embodied integrally with the main washing element body 66, conduits 12a, 12b are formed which, like the conduit 12 that serves the purpose of washing out, communicate with the inner region of a breathing mask and furthermore discharge into the hose connection stubs 41, 42 described in conjunction with FIG. 3a. The interstice formed by this double-walled structure 5 in this respect furnishes a conduit system by way of which a diversion of $CO_2$-laden breathing gas, a pressure measurement, and additional delivery of oxygen, or air sampling, for instance for analysis of the breathing gas, can be accomplished.

Figure 4A:
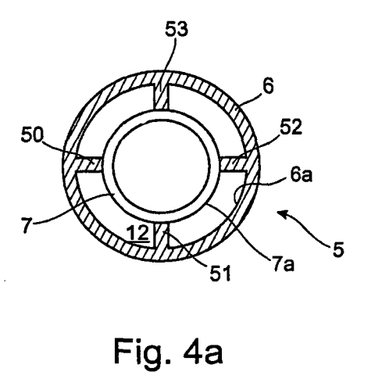
FIG. 4a, another radial sectional view for explaining the principle of the flow conduits furnished by a double-walled structure.

In FIG. 4a, a variant of this double-walled structure 5 is shown, in which the interstice or intermediate conduit 12 furnished between the walls 6a, 7a is subdivided into a plurality of longitudinal conduits by a plurality of longitudinal ribs 50, 51, 52, 53. The sleeve element 7 is inserted into the tubular stub portion 6. The aforementioned ribs 50, 53 are embodied integrally with the tubular stub portion 6 in this exemplary embodiment.

Figure 4B:
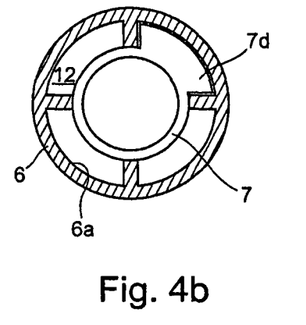
FIG. 4b, a radial sectional view for explaining a variant with a partially blocked conduit segment for reducing the flow cross section.

FIG. 4b shows a variant in which the sleeve element 7 is provided with a blocking rib 7d, by which the cross section of the conduit 12 that is intended for the diversion of the $CO_2$-laden breathing gas can be reduced. For defining the breathing gas outflow, it is possible to embody the sleeve element 7 such that it blocks a plurality of sections of the conduit. It is also possible to form ribs on the sleeve element that form labyrinths and that, in collaboration with the inner wall 6a of the tubular stub portion 6, form flow paths with the defined flow resistance.

Figure 5:
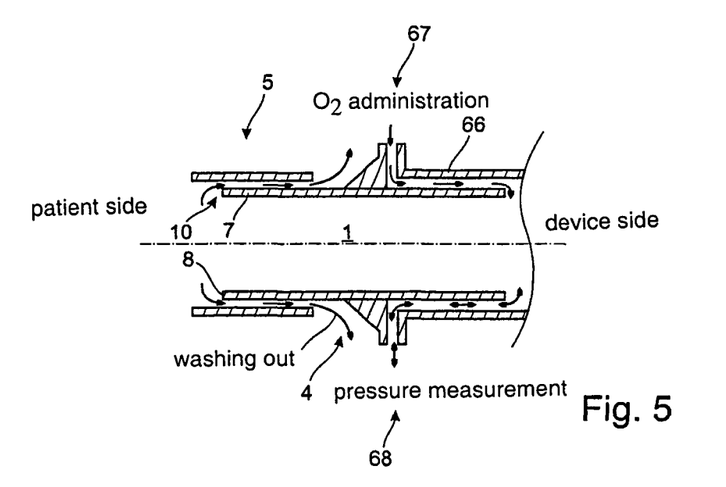
FIG. 5, an axial sectional view of a further exemplary embodiment of an arrangement according to the invention for diverting $CO_2$-laden breathing gas.

In FIG. 5, a further embodiment of a device according to the invention is shown, highly simplified, in which device, using a double-walled structure 5, an axial offset is attained between an inlet gap region 10 and an outlet orifice portion 4, and in which furthermore the inlet gap region 10 is located at the level of a terminal circumferential face 8 of the tubular stub structure that defines the breathing gas conduit 1. In this exemplary embodiment as well, the main washing element body 66 is provided with connection structures 67, 68, by way of which a delivery of gas or a diversion of gas and in particular also a pressure measurement can be accomplished. The conduits used for this purpose and provided in the region of the breathing gas delivery system that is at an elevated pressure level compared to the ambient pressure are formed, in this exemplary embodiment as well, by the use of a sleeve element 7 in collaboration with an inner circumferential wall of the main washing element body 66.

The invention is not limited to the exemplary embodiments described above. For instance, it is also possible to embody the main washing element body 66 as part of a hard shell of a breathing mask, so that the main washing element body 66, and in particular its rotary bearing portion 20 intended for receiving the rotation cuff 14, form an integral component of the hard breathing-mask shell. The sleeve element 7 can be thrust into the main washing element body 66 either from the interior of the shell body of the mask or preferably also from the hose-side end. It is also possible to embody the sleeve element 7 integrally with the rotation cuff 14, i.e. to combine the sleeve element 7 and the rotation cuff 14 into a single part.

In the region of the outflow portion 4, air guide structures, in particular ribs, lamellae, or caverns, that deviate from the exemplary embodiments described above, may also be provided. It is also possible, in the region of the outflow portion 4, to provide elastomer structures by which the occurrence of any flow noises can be further prevented. The sleeve element 7 may also be made from a porous material, so that particularly in addition to the entrance of the air to, be diverted via the inlet gap region 10 (FIG. 1), an entrance of air into the region of the outflow portion or of the conduit 12 can be effected through the wall of the sleeve element 7.

The device according to the invention may alternatively, or in combination with a rotation cuff device, also be provided with a hinge device by means of which tilting motions of the hose relative to the main washing element body 66 are made possible about axes that are oriented essentially perpendicular to the longitudinal axis X of the main washing element body. The individual components of the device according to the invention may be manufactured in particular from a relatively rigid thermoplastic material. It is also possible to manufacture the main washing element body 66, in particular, from a hard elastic material.

Figure 6:
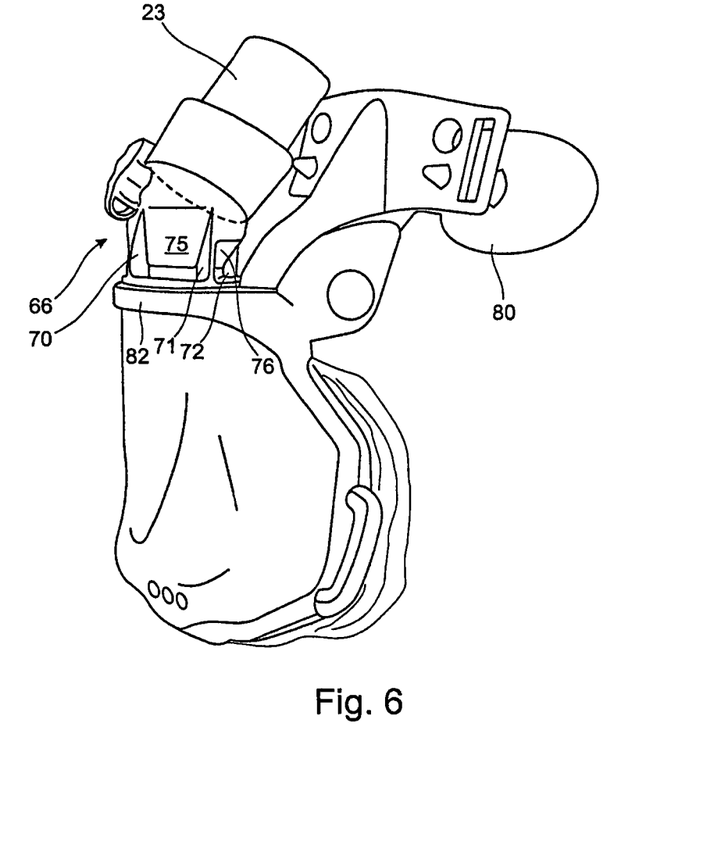
FIG. 6, a perspective view of a breathing mask according to the invention, with a goose-necked (hose connection) line element that furnishes an integrated $CO_2$ diversion path.
Figure 7:
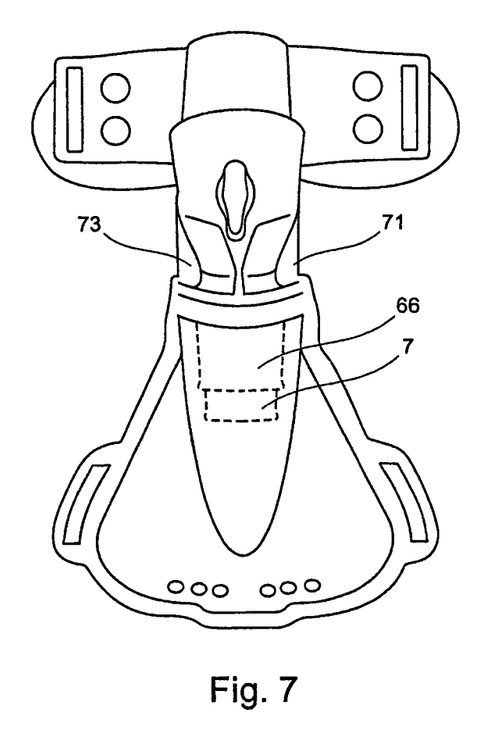
FIG. 7, a top view onto the breathing mask of FIG. 6 for further illustrating structural characteristics of the breathing mask, in particular with regard to the goose-necked line element.
Figure 8:
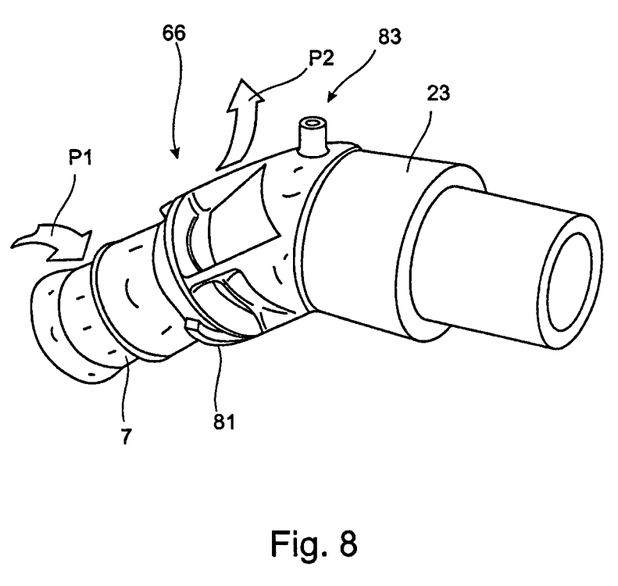
FIG. 8, a perspective view of the line element, embodied in multiple parts, of the breathing mask of FIGS. 6 and 7.

For the breathing mask of FIGS. 6 and 7 and the line element of FIG. 8, the above descriptions apply accordingly. For details and components of the breathing mask and line element that have already been addressed per se in conjunction with FIGS. 1 through 5, the same reference numerals will be used, in part without addressing these components again.

In the breathing mask of FIGS. 6 and 7, the main washing element body 66 is embodied in goose-necked fashion. The angle of the bend is in the range of 25 to 60°, and is preferably approximately 30°.

In the region of the outflow orifice portion 4, there are four longitudinal ribs 71, 72, 73 (the fourth cannot be seen in this view). The main washing element body 66, on its side facing away from the user in the application position, forms a ramp zone 75 that is shallow in terms of the oncoming flow direction. The ramp zone 75 in this exemplary embodiment is divided by the longitudinal rib 70 and is also enclosed by the rib 71 and the diametrically opposed rib 73 (FIG. 7). Advantageous air guidance is achieved by this enclosure by means of the ribs 71 and 73.

The main washing element body 66 is provided with a steeper ramp zone 76, on a side of the main washing element body that faces toward the user in the application position of the breathing mask. It is possible to take precautions such that a lesser air stream flows away via this ramp zone than via the ramp zone 75. It is also possible to achieve a complete blockage here.

The hose mounting stub 23, already mentioned above, is seated on the main washing element body 66 in a manner supported rotatably movably about its tube axis.

The breathing mask shown here is distinguished in particular by the fact that a diversion of the $CO_2$-laden breathing gas takes place in a region of the mask which, in the application position, is located approximately at the level of the bridge of the user's nose, or at least below the region in which the mask is braced on the forehead of the patient (for instance via the forehead pads 80).

Because of the special design of the main washing element body 66 and the use of the sleeve element 7 (FIG. 1), it becomes possible to carry air away with only little clearance.

FIG. 8 shows in the form of a perspective view the main washing element body 66 with the hose connection stub 23 attached and with the sleeve element 7. The main washing element body 66 is provided with a securing structure 81, by way of which it can be coupled to a frame portion 82 (FIG. 6) of the breathing mask. The securing structure 81 here comprises two bayonet flanks which can be brought into engagement with a correspondingly complementary counterpart structure in the frame portion 82.

In the mounted state, the main washing element body 66 protrudes, similarly to what is shown in FIG. 2, into the mask interior with its part protruding past the frame portion 82, and in particular with the sleeve element 7. An air diversion (arrow symbol P1) is effected via the gap region formed between the outer circumferential surface of the sleeve element 7 and the inside surface of the main washing element body 66, which region is shielded off as such from the actual air delivery path. The air entering the gap flows away to the environment via the ramp zone 75 (arrow symbol P2).

In its outward-pointing knee region, the main washing element body 66 is provided with a connection structure 83, which is embodied here as a measurement hose connection stub. Via this structure, a pressure or gas measurement can be made, and/or an active infeed of oxygen or other gas can be done. In FIGS. 6 and 7, this structure is covered with a cap.

The invention claimed is:

1. A diversion device for diverting breathing gas which is laden with $CO_2$ from an overpressure region of an arrangement that includes a breathing mask and serves to deliver a breathing gas at a pressure level that is above the ambient pressure, having:
    a tubular stub structure, which defines a breathing gas conduit that extends between an inlet cross section on a hose side and an outlet cross section on a mask side, and which is provided, in a region located between the inlet cross section and the outlet cross section, with an outflow orifice portion, by way of which the breathing gas to be carried reaches the environment,
    wherein, in a region located between the outflow orifice portion and the outlet cross section on the mask side of the breathing gas conduit and spaced from a terminal circumferential face of the outlet cross section by a gap region, a double-walled structure that surrounds the breathing gas conduit is embodied for sampling the breathing gas to be carried away from a mask interior, while an inlet region leading to the double-walled structure is located outside the breathing gas conduit.

2. The device as defined by claim 1, characterized in that the double-walled structure is formed with the inclusion of a sleeve element.

3. The device as defined by claim 2, characterized in that the sleeve element is inserted into a tubular stub portion of a main washing element body.

4. The device as defined by claim 3, characterized in that the sleeve element is placed onto the main washing element body.

5. The device as defined by claim 3, characterized in that the sleeve element and the main washing element body are embodied such that the sleeve element protrudes axially past the main washing element body in the region of the mask-side outlet cross section to define the gap region.

6. The device as defined by claim 3, characterized in that the sleeve element and the main washing element body are detachably coupled to one another.

7. The device as defined by claim 3, characterized in that the main washing element body is provided with a rotary adapter structure, for rotatably movably supporting a rotation cuff.

8. The device as defined by claim 1, characterized in that in the region of the double-walled structure, air guide structures are embodied, which produce a required flow resistance.

9. The device as defined by claim 8, characterized in that the air guide structures are embodied as labyrinth structures.

10. The device as defined by claim 1, characterized in that the double-walled structure defines a conduit with a radial gap height in the range from 0.3 to 3.2 mM.

11. The device as defined by claim 1, characterized in that in cooperation with the double-walled structure, adjusting devices are accomplished for adjusting the flow resistance.

12. The device as defined by claim 1, wherein the inlet region is formed along an exterior portion of the breathing gas conduit.

13. A breathing mask arrangement having a mask interior defined by a basic mask body and a sealing lip device, wherein the basic mask body has a connection portion receiving a tubular stub structure which defines a breathing gas conduit that extends between an inlet cross section on a hose side and an outlet cross section on a mask side, and which is provided, in a region located between the inlet cross section and the outlet cross section, with an outflow orifice portion by way of which the breathing gas to be carried reaches the environment, wherein, in a region located between the outflow orifice portion and the outlet cross section on the mask side and spaced from a terminal circumferential face of the outlet cross section by a gap region, a double-walled structure that surrounds the breathing gas conduit is embodied for sampling the $CO_2$-laden breathing gas to be carried away, wherein an inlet region leading to the double-walled structure is positioned within the mask interior, such that the $CO_2$ laden breathing gas can flow directly into the inlet region substantially without being conveyed within the breathing gas conduit in use.

14. The breathing mask arrangement as defined by claim 13, characterized in that the tubular stub structure is seated in the region of the double-walled structure in the connection portion of the basic mask body.

15. A breathing mask for a breathing mask arrangement as defined by claim 13.

16. The breathing mask arrangement as defined by claim 13, wherein the double-walled structure includes a sleeve that extends into the mask cavity and includes an outer cylindrical surface along which the $CO_2$ laden gas travels in use.

* * * * *

UNITED STATES PATENT AND TRADEMARK OFFICE
CERTIFICATE OF CORRECTION

PATENT NO. : 8,496,004 B2
APPLICATION NO. : 11/632667
DATED : July 30, 2013
INVENTOR(S) : Lang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1307 days.

Signed and Sealed this
Fifteenth Day of September, 2015

Michelle K. Lee
*Director of the United States Patent and Trademark Office*